United States Patent
Vellutato, Sr.

(10) Patent No.: US 10,729,795 B2
(45) Date of Patent: Aug. 4, 2020

(54) METHOD FOR MIXING AND DISPENSING

(75) Inventor: Arthur L. Vellutato, Sr., Exton, PA (US)

(73) Assignee: Veltek Associates, Inc., Malvern, PA (US)

( * ) Notice: Subject to any disclaimer, the term of this patent is extended or adjusted under 35 U.S.C. 154(b) by 456 days.

(21) Appl. No.: 10/754,629

(22) Filed: Jan. 12, 2004

(65) Prior Publication Data
US 2005/0163651 A1    Jul. 28, 2005

(51) Int. Cl.
*A61L 2/02* (2006.01)
*B65B 55/16* (2006.01)
*A61L 2/08* (2006.01)

(52) U.S. Cl.
CPC ............... *A61L 2/022* (2013.01); *A61L 2/08* (2013.01); *B65B 55/16* (2013.01)

(58) Field of Classification Search
USPC .......................................................... 422/22
See application file for complete search history.

(56) References Cited

U.S. PATENT DOCUMENTS

| | | |
|---|---|---|
| 2,781,141 A | 2/1957 | Lucien |
| 3,156,369 A | 11/1964 | Bowes et al. |
| 3,326,400 A | 6/1967 | Hamelin et al. |
| 3,347,410 A | 10/1967 | Schwartzman |
| 3,458,076 A | 7/1969 | Babcock |
| 3,856,138 A | 12/1974 | Maekawa et al. |

(Continued)

FOREIGN PATENT DOCUMENTS

| | | |
|---|---|---|
| AU | 2005202466 A1 | 1/2006 |
| DE | 460 043 | 5/1928 |

(Continued)

OTHER PUBLICATIONS

USP 26, General Information/(1211) Sterilization and Sterility Assurance of Compendial , pp. 2433-2438, 2003.

(Continued)

*Primary Examiner* — Kevin Joyner
(74) *Attorney, Agent, or Firm* — Blank Rome LLP

(57) ABSTRACT

A method for sterilizing a concentrated composition and a diluent. The diluent is contained in a large container, and the concentrated composition is contained in a small container that is positioned within the large container. The combined containers are placed in at least one sealing layer that is hermetically sealed, and is also preferably placed in a second sealing layer that is also hermetically sealed. The bagged container is then placed in a carton, which preferably has a liner, and the carton is closed. The carton is then irradiation sterilized. The carton is delivered to the clean room. At a first staging area, the carton is opened and the bagged container is removed and brought to a second staging area. At the second staging area, the second sealing layer is removed and the container can be stored in the first sealing layer. The container is brought into the clean environment, where the first sealing layer is removed. At that point, the small container is opened and the chemical composition is released into the large container, so that the chemical composition mixes with the diluent. The container can then be shaken until the chemical composition is thoroughly mixed with the diluent.

46 Claims, 4 Drawing Sheets

(56) References Cited

U.S. PATENT DOCUMENTS

| | | | |
|---|---|---|---|
| 3,966,089 A | 6/1976 | Klingaman | |
| 3,968,872 A | 7/1976 | Cavazza | |
| 4,177,938 A | 12/1979 | Brina | |
| 4,195,730 A | 4/1980 | Hunt | |
| 4,195,731 A | 4/1980 | Cavazza | |
| 4,221,291 A | 9/1980 | Hunt | |
| 4,264,007 A | 4/1981 | Hunt | |
| 4,591,050 A | 5/1986 | Finke et al. | |
| 4,615,437 A | 10/1986 | Finke et al. | |
| 4,757,916 A | 7/1988 | Goncalvaes | |
| 4,793,475 A | 12/1988 | Itzel | |
| 4,832,230 A | 5/1989 | Janowitz | |
| 4,903,865 A | 2/1990 | Janowitz | |
| 4,981,238 A | 1/1991 | Wenmaekers | |
| 4,982,875 A | 1/1991 | Pozzi et al. | |
| 5,029,718 A | 7/1991 | Rizzardi | |
| 5,038,951 A | 8/1991 | Rizzardi | |
| 5,114,011 A | 5/1992 | Robbins, III | |
| 5,215,225 A | 6/1993 | Kopp | |
| 5,383,579 A | 1/1995 | Lanfranconi et al. | |
| 5,421,483 A | 6/1995 | Parise | |
| 5,538,508 A * | 7/1996 | Steyn | 604/192 |
| 5,543,097 A | 8/1996 | Fang | |
| 5,613,623 A | 3/1997 | Hildebrandt | |
| 5,772,017 A | 6/1998 | Kang | |
| 5,811,080 A | 9/1998 | Valderrama | |
| 5,860,569 A | 1/1999 | Gregoire | |
| 5,875,889 A | 3/1999 | Albisetti | |
| 5,941,380 A | 8/1999 | Rothman | |
| 5,950,819 A | 9/1999 | Sellars | |
| 6,022,134 A | 2/2000 | Andrew | |
| 6,041,969 A | 3/2000 | Parise | |
| 6,073,803 A | 6/2000 | Sturm et al. | |
| 6,123,900 A * | 9/2000 | Vellutato | 422/22 |
| 6,150,423 A * | 11/2000 | Carpenter | 514/731 |
| 6,152,296 A | 11/2000 | Shih | |
| 6,305,576 B1 | 10/2001 | Leoncavallo | |
| 2004/0140321 A1 | 7/2004 | Stank et al. | |

FOREIGN PATENT DOCUMENTS

| | | |
|---|---|---|
| DE | 20022904 | 8/2002 |
| EP | 0300886 A1 | 1/1989 |
| EP | 0999149 A1 | 5/2000 |
| FR | 2707601 | 1/1995 |
| GB | 2280657 B | 2/1995 |
| GB | 2317870 A | 4/1998 |
| JP | 1990/048546 | 4/1990 |
| KR | 10-20100122825 | 11/2010 |
| WO | WO 02/085 775 | 10/2002 |

OTHER PUBLICATIONS

Clean Rooms, Sterile Contact Plate, Becton Dickinson Microbiology Systems, Cockeysville, MD, Jun. 1991.

Clean Rooms, vol. 5, No. 3, BBL Sterile Contact Plate, Becton Dickinson Microbiology Systems, Cockeysville, MD, Mar. 1991.

Search Report and Written Opinion for SG Application No. 10201606357, dated May 3, 2019, 11 pgs.

Korean Office Action for KR Application No. 10-2015-0182034, dated Sep. 18, 2018, 6 pages.

English-language Summary of Korean Office Action for KR Application No. 10-2015-0182034, dated Sep. 18, 2018, 1 page.

* cited by examiner

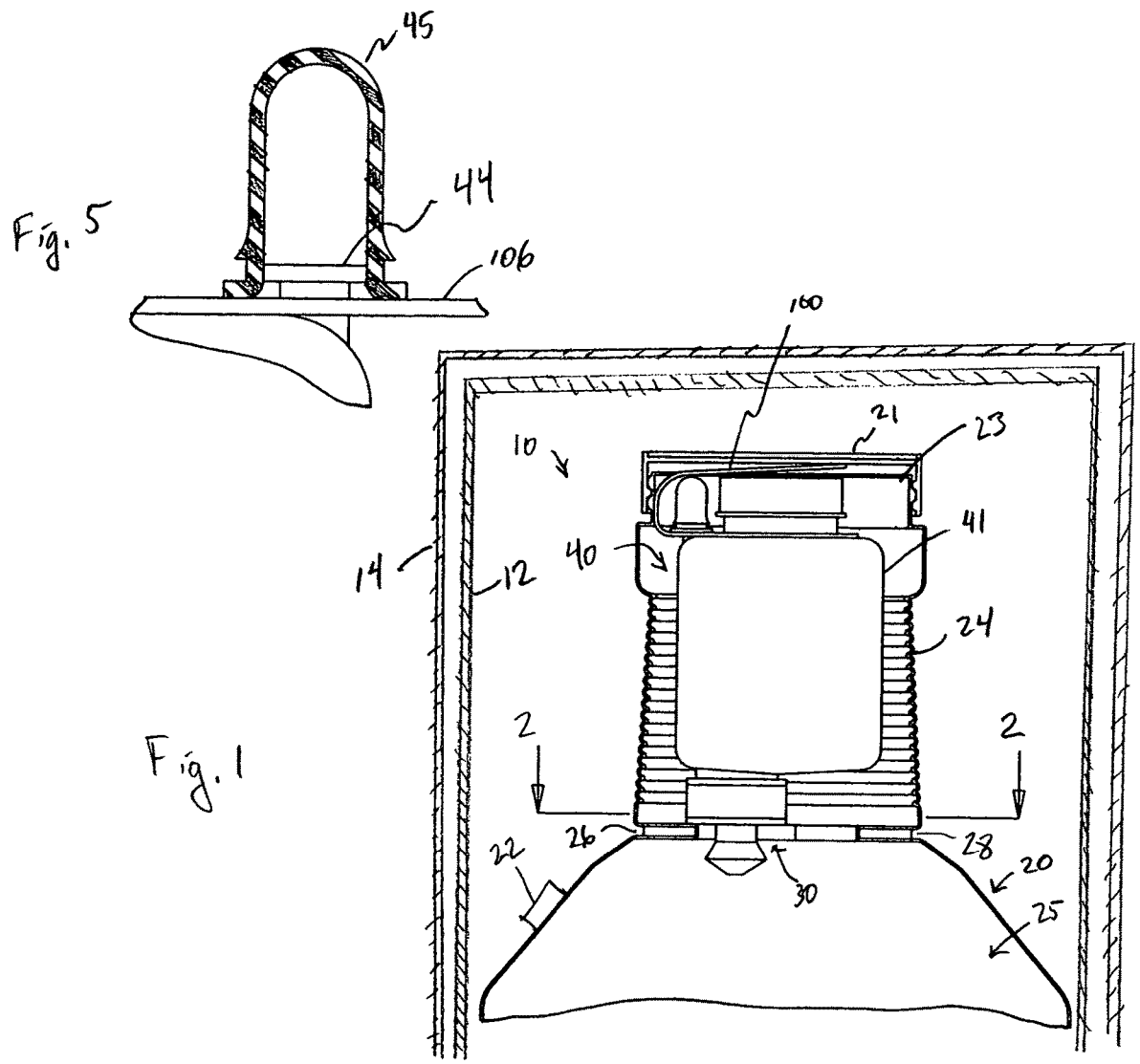
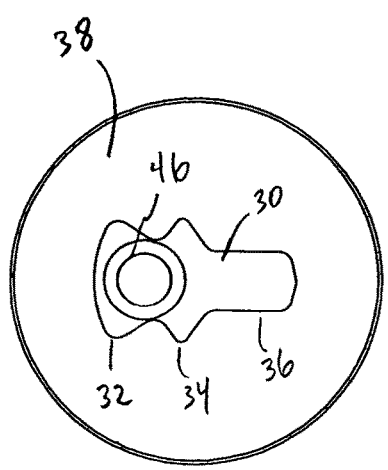

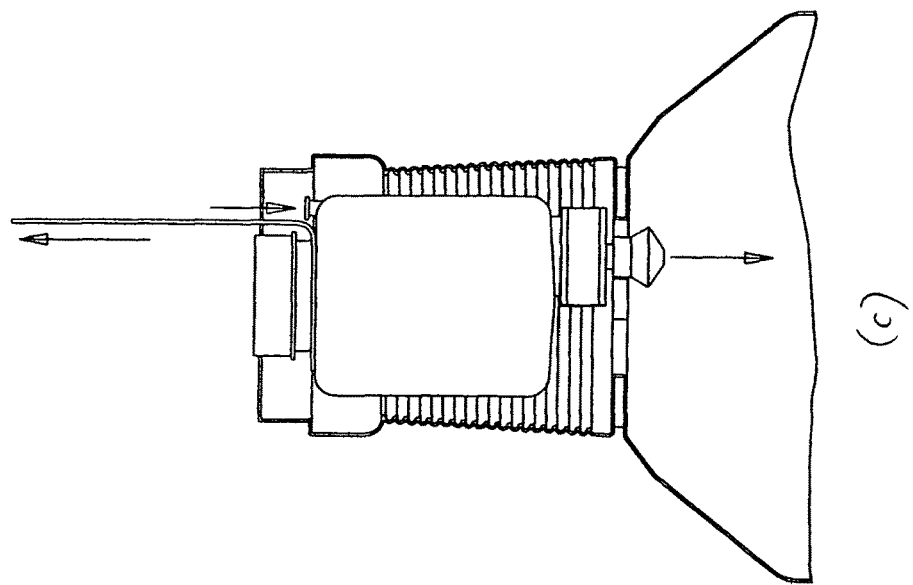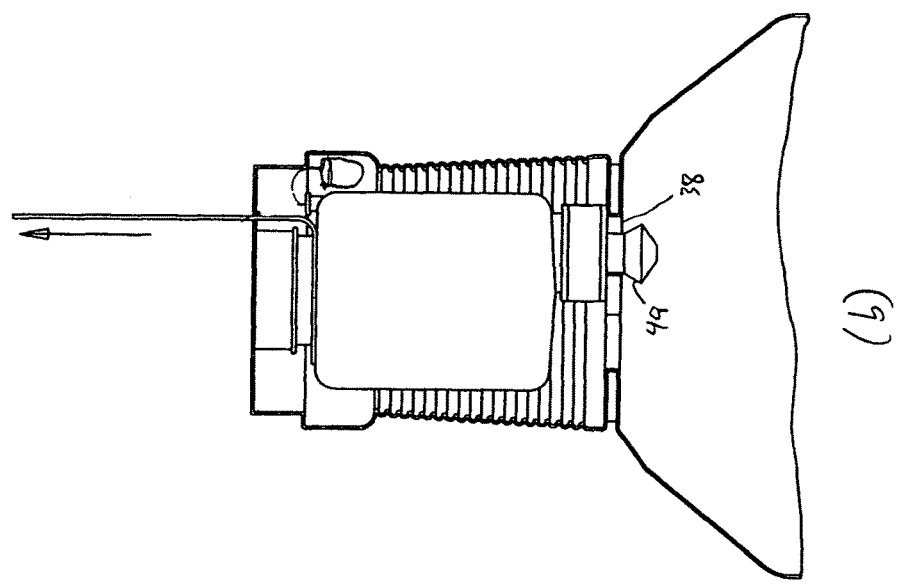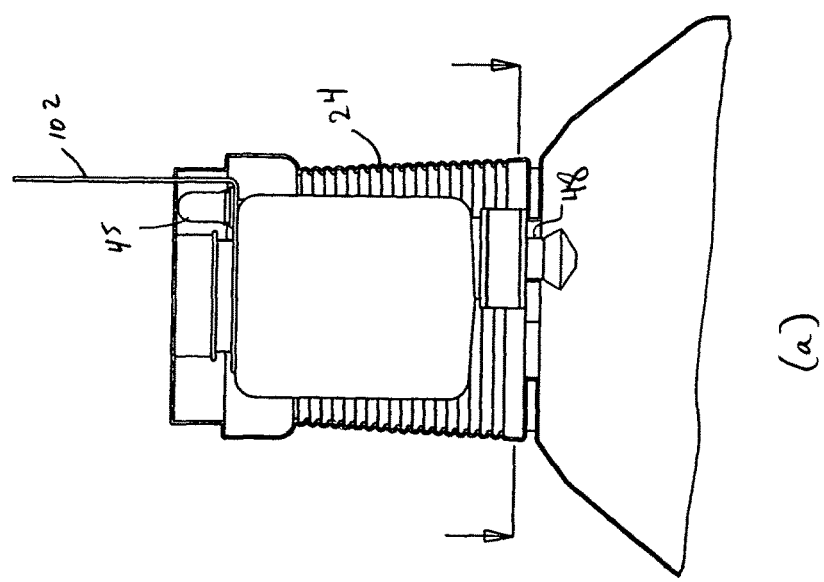
Fig. 6

METHOD FOR MIXING AND DISPENSING

BACKGROUND OF THE INVENTION

Field of the Invention

The present invention relates to a method for sterilizing a concentrated composition contained within a closed container so as to permit dilution and mixing of the composition and a diluent, especially in an aseptic or sterile environment.

Background of the Related Art

A clean room is a space designed, maintained, and controlled to prevent particle and microbiological contamination of products. Certain chemical compositions are used inside clean rooms including, for instance, germicidal disinfectants such as phenols, cleaners, quaternary ammonium, peracetic acid, as well as various sporicides, such as peracetic acid, bleach, and hydrogen peroxide. The disinfectants and sporicides are used in clean rooms to disinfect clean room surfaces. The compositions, which are not naturally sterile, can be sterilized by filtration inside of the clean room.

To sterilize the compositions outside the clean room, the concentrated composition is either terminally sterilized by irradiation or aseptically processed. To terminally irradiation sterilize the composition, the composition is placed in a container, double bagged, and placed in a lined carton. The entire carton is then terminally sterilized by irradiation. A procedure for terminally irradiation sterilizing a composition is described, for instance, in U.S. Pat. No. 6,123,900 to Vellutato, the disclosure of which is incorporated herein by reference.

To aseptically process the concentrated composition, the composition is sterilized through filtration and (inside a sterile environment) placed into a container that has been pre-sterilized, such as by irradiation. The container can then be double bagged, also within the sterile environment. The double-bagged package is then removed from the sterile environment and placed into a carton having a liner. Aseptic processing is generally more labor intensive and expensive than terminal irradiation sterilization, and is typically only used for chemicals that cannot be irradiation sterilized, such as peracetic acid and hydrogen peroxide.

When concentrated compositions are used, they first must be diluted with sterile water to the proper concentration for use. However, the dilution breaks down the compositions, and consequently the diluted compositions have a relatively short shelf life of between about 17-30 days. Accordingly, clean room personnel typically dilute the concentrated composition just prior to actual use. To do so, once the sterile concentrated composition enters the clean room (either through on-site filter sterilization, or off-site irradiation sterilization or aseptic processing), it is typically manually mixed with a diluent (i.e., the sterile water) in a sterile container, such as a bucket, inside the clean room. The dilution and mixing has to be precise to ensure that the resulting concentration of disinfectant or sporicide will effectively kill the desired microorganisms. The mixing is difficult to perform manually since the person performing the mixing is outfitted in clean room apparel, such as sterile garments and gloves. Accordingly, the mixing is a time-consuming process that detracts from the time being spent on other work being performed in the clean room.

SUMMARY OF THE INVENTION

Accordingly, it is an object of the invention to provide a method for sterilizing more than one composition that also facilitates mixing of the compositions in a sterile environment. It is another object of the invention to provide a method for sterilizing a composition that provides for mixing of the composition with a diluent in a sterile container system that is not affected by the external environment.

In accordance with these and other objectives, the present invention is a method for sterilizing a concentrated composition and a diluent. The diluent is filtered at 0.2 microns and contained in a large container. The concentrated composition is filtered at 0.2 microns and contained in a small container that is positioned within the large container of diluent. The combined containers are placed in at least one sealing layer or bag that is hermetically sealed, and is also preferably placed in a second sealing layer or bag that is also hermetically sealed. The sealed or bagged container is then placed in a carton, which preferably has a liner, and the carton is closed. The carton is then irradiation sterilized.

The irradiation-sterilized carton is then delivered to a clean room. At a first staging area, the carton is opened and the bagged container is removed and brought to a second staging area. At the second staging area, the second sealing layer is removed and the container can be stored in or adjacent the second staging area in the first sealing layer. When a container is to be used, it is transported in the first sealing layer into the clean room environment, where the first sealing layer is removed. The small container is then opened and the chemical composition is released into the large container so that the concentrated chemical composition is mixed with and diluted by the diluent. The large container can then be agitated or shaken until the chemical composition is thoroughly mixed with the diluent.

These and other objects of the invention, as well as many of the intended advantages thereof, will become more readily apparent when reference is made to the following description, taken in conjunction with the accompanying drawings.

BRIEF DESCRIPTION OF THE DRAWINGS

FIG. 1 is a partial side elevation view, partly in section, showing the mixing and dispensing container placed in first and second sealing layers in accordance with a preferred embodiment of the method of the invention;

FIGS. 2(a) and 2(b) are cross-sectional views taken along line 2-2 in FIG. 1 showing an opening formed at the junction of the large and small containers used in the preferred embodiment of the method of the invention;

FIG. 5 is a fragmentary side elevation view, partly in section, showing a rubber cap installed on the small container of FIG. 1;

FIGS. 6(a)-6(c) are partial side elevation views, partly in section, showing the sequence of steps for releasing of the contents of the small container into the large container;

DETAILED DESCRIPTION OF THE PREFERRED EMBODIMENTS

Figures 3, 4:
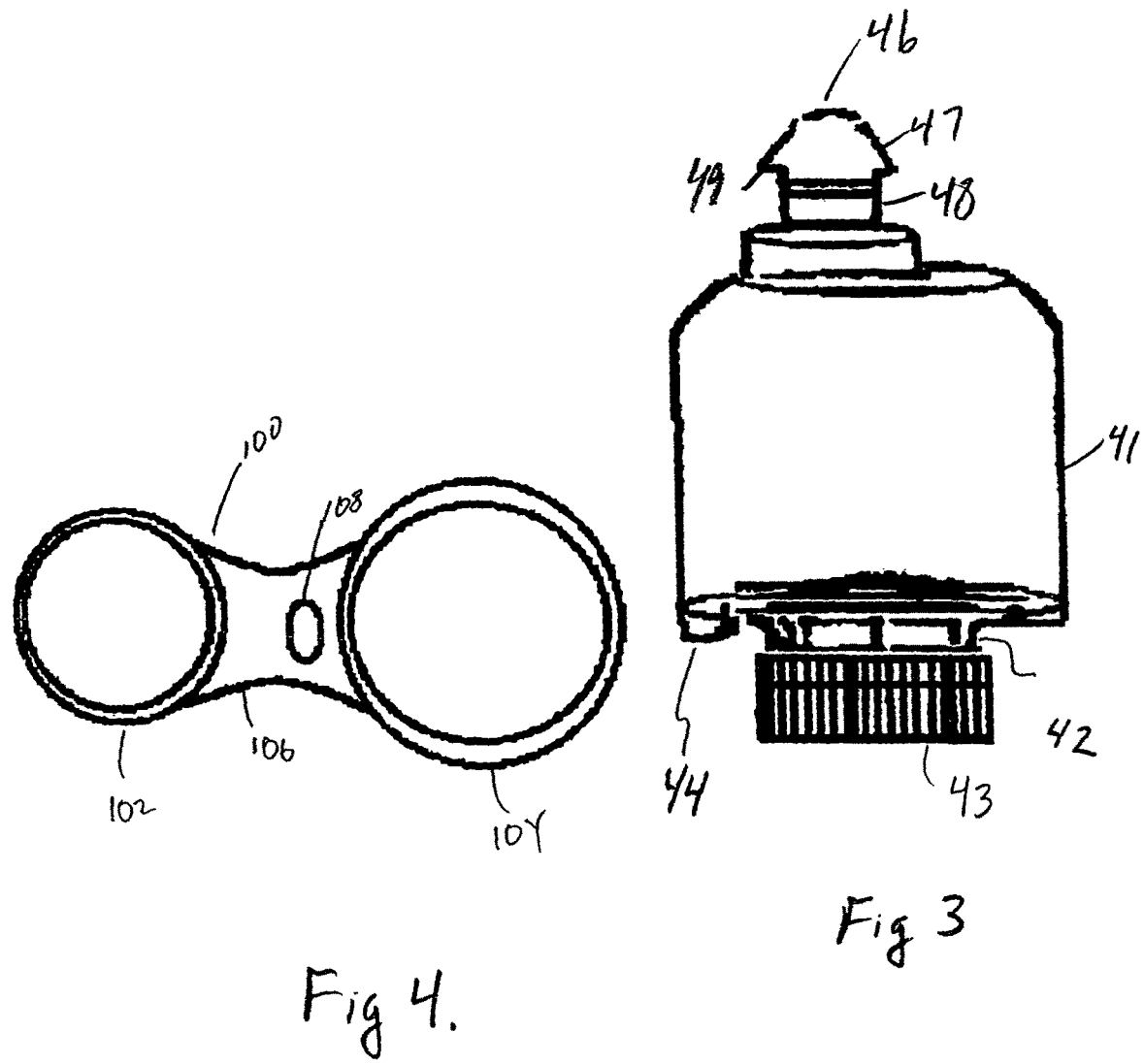
FIG. 3 is a side elevation view of the small container of FIG. 1.
FIG. 4 is a plan view of a ring pull device for use with the small container of FIG. 1.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose.

Turning to the drawings, FIG. 1 shows a mixing and dispensing apparatus 10 used in accordance with the preferred embodiment of the method of the invention. The apparatus is described in U.S. patent application Ser. No. 10/346,169, the disclosure of which is incorporated herein by reference. It should be noted that any mixing and dispensing apparatus could be used in the method of the invention, though the apparatus shown and described in the present specification can be used in the practice of the preferred embodiment of the method invention.

The apparatus 10 has two primary elements: a first large container 20, and a second small container 40. The large container 20 and the small container 40 are both preferably round plastic bottles, and are sized so that the small container 40 can be positioned inside a chamber of the large container 20. The small container has a normally closed nozzle or spout 46 at one end thereof for discharging the contents of the small container into the large container according to the method of the invention. The large container 20 has a ribbed neck 24, and an opening 23 at the top of the neck adapted to be closed by a removable cap 21, such as a threaded cap. The large container 20 is provided with a reservoir 25 that is used to retain a first substance, e.g., a diluent. The neck 24 forms a chamber that receives the second container 40, and the opening 23 permits the small container 40 to be introduced into and positioned inside the neck 24. The reservoir 25 of the large container 20 holds a predetermined amount of diluent, preferably about 1 gallon of sterile water, for use in the method of the invention.

As shown, the neck 24 of large container 20 has an annular depression 26 that forms a plate or platform 38 through which passes a narrowed passageway 30 so as to provide an opening into the container reservoir 25 from the chamber of neck 24. The small container 40 is placed in the neck 24 of the large container 20 through opening 23, and the nozzle 46 of the small container is positioned in the passageway 30. The nozzle 46 of the small container 40 can then be opened by pulling upwardly on the neck 24 and small container, so that the bottom surface of the platform 38 engages a portion of the nozzle and urges the nozzle to its open position. The top surface of platform 38 supports the small container 40 in the chamber of neck 24. Flexible foam can also be positioned in the chamber about the small container 40 to stabilize it within the neck 24, especially during transportation.

Turning to FIGS. 2(a) and 2(b), the manner in which the small container 40 engages the internal passageway 30 of the large container 20 is shown. As previously mentioned, the annular depression 26 preferably forms an internal passageway 30 in the platform 38. Passageway 30 has a generally keyhole shape with a wide portion 32, a narrow portion 36, and an intermediate portion 34 therebetween. As shown in FIG. 1, the nozzle 46 is off-centered with respect to the body 41 of the small container 40. Accordingly, the small container 40 can be placed inside the neck 24 of the large container 20 with the container 40 oriented so that the nozzle 46 is aligned with the wide portion 32 of the passageway 30.

When inserted into the chamber of the neck 24, the small container 40 is lowered so that the nozzle 46 passes into the wide portion 32 of the passageway 30. At that point, the small container 40 is not rigidly fixed to the large container 20. The small container 40 is then given a quarter turn, at which point the nozzle 46 of the small container enters the mid-portion 34 of the passageway 30. The widened intermediate portion 34 operates as a transition area to give the small container 40 some stability within the passageway 30 so that the small container does not fall over within the neck of the large container 20. The small container 40 can then be straightened or flexible foam pieces may optionally be inserted around the small container to further stabilize the small container within the neck 24 of the large container 20.

The small container 40 is then rotated another quarter turn, so that the neck portion 48 of the nozzle cap 47 of the small container 40 moves into a fixed position at the narrow portion 36 of the passageway 30, where it essentially becomes locked in place. When the small container 40 is pulled axially outwardly, the bottom surface of platform 38 grips shoulder 49 of the nozzle cap 47, which in turn pulls the nozzle cap outwardly to open the nozzle 46 and allow the substance in the small container 40 to dispense into the reservoir 25 of the large container 20. It should be recognized that the passageway 30 may have any suitable size and shape, such as a circular shape, an may operate by a frictionally fit with the nozzle, though the passageway 30 is preferably shaped to engage the nozzle without allowing the nozzle to fully withdraw from the large container.

The large container 20 has a pour spout 22, which is preferably located at one side thereof. Thus, the contents of the large container 20 may be dispensed through the pour spout 20 without obstruction.

FIG. 3 shows the small container 40. The small container 40 has an opening with a tapered collar 42 which projects outwardly from the bottom surface of the small container. A cover or cap 43 closes vent or opening 44 that is also located on the bottom surface of the container. The cap 43 can optionally be one that is capable of venting gas from corrosive or volatile liquids (such as peracetic acid and Hydrogen peroxide), without allowing liquid to escape. As previously described, the neck of the small container 40 is off-center to make it easier to position the nozzle 46 within the internal passageway 30. It should be understood, however, that the neck can be any suitable size, and may also be centered, i.e., aligned with the axis of the small container.

The nozzle arrangement 46 of the small container 40 is also shown in FIG. 3. The nozzle 46 has a generally frusto-conical nozzle cap 47, a cylindrical neck 48, and an annular shoulder 49 formed therebetween. The nozzle 46 is preferably opened and closed by pulling and pushing, respectively, on the nozzle cap 47. Thus, when the nozzle cap 47 is pulled axially outwardly, i.e., away from the small container, the nozzle 46 is opened and, with the container in the position shown in FIG. 1, the contents of the small container 40 are dispensed into the large container 20. When the nozzle cap 47 is pushed inwardly, i.e., toward the small container, the nozzle 46 is closed, and the contents of the small container 40 are sealed in the container 40.

Referring to FIG. 4, a pull 100, which is made of polypropylene or polyester, is provided for use with the small container 40. The pull 100 has two different diameter rings 102, 104 connected by a mid-section 106. The larger ring 104 is placed about the tapered collar 42, and the cover 43 is then placed on the collar to close the container. The mid-section 106 has an opening 108 that fits over the vent 44 of the small container 40.

A cap or cover 45, which can be made of rubber or any other suitable material, is placed over and closes the vent 44, as best shown in FIG. 5. After the large ring 104 is placed around the collar 42, the opening 108 is fitted over the vent 44 on the container. The rubber cover 45 is then placed over the vent 44, to prevent the composition from escaping the small container. The pull 100 is then folded at the midsection 106, so that the small ring 102 is located at the top of the cap 43 (FIG. 1). The pull 100 goes over the cover 45 so that the cover 45 will stay with the pull inside the large container 20 when it is pulled by the user. The small ring 102 is a finger grip that can be gripped and pulled by a user.

Turning to FIGS. 6(a)-(c), the operation of the pull 100 is illustrated as follows. As shown in FIG. 6(a), the cap 21 is removed from the large container 20, and the small ring 102 comes free of the large container. At FIG. 6(b), the user pulls the small ring 102 upwardly and away from the large container. The outer portion of the neck 24 is ribbed to facilitate the user gripping the container 20 and pulling on the pull 100. The pulling action causes the rubber cover 45 to be pulled off of the vent 44 in the small container. The rubber cover 45 is trapped between the pull and the cap 43 so that the cover 45 does not fall into the sterile environment. The pulling action also causes the large ring 104 to press upwardly against the lip on the cap 43 fastened to collar 42, so that the entire small container 40 is pulled upwardly. The shoulder 49 of the nozzle 46 engages the bottom surface of the platform 38, thereby urging the nozzle of the small container to its open position.

As shown in FIG. 6(c), the nozzle is opened, and the contents of the small container dispense into the reservoir of the large container. The vent 44 is open thereby allowing air to enter the small container and permit the concentrated composition to more easily dispense from the small container into the large container. Because the nozzle cannot pass through the narrowed portion 36 of the passageway 30, the small container stays within the neck 24 of the large container. The small ring 102 is then folded down, and the cap 21 is replaced over the opening 23 of the large container, with the small container 40 and vent cover remaining inside.

In operation, the diluent and the chemical composition are assayed separately to ensure that proper formulations have been received. The composition and diluent are filtered with a 0.2 micron filter to remove particulates, and a particulate test is conducted. The composition and diluent are then measured to ensure that the proper dilution will result when they are eventually mixed together.

The large container and small container are filled in two separate operations so that there is no accidental mixture of chemical agents. Sterile water is filtered at 0.2 microns into the reservoir 25 of the large container. A concentrated chemical composition, such as a disinfectant, is filtered at 0.2 microns into the small container. Upon completion of filling of the small container with the second substance through the opening in collar 42, and with the pull 100 and vent cover 45 in place, the opening is closed with cap 43. The small container is then placed into the neck 24 at the top of the large container and the nozzle 46 is engaged with the passageway 30 as shown in FIG. 2(b). The top of the large container is then closed with cap 21 and the product labeled, bagged, and placed in an optionally lined carton.

The large container 20 is filled with the first substance, the diluent, either through the spout 22 or the top opening 23. If the top opening 23 is used, the large container 20 is filled before the small container 40 is placed in the neck 24 as described above. The contents of the containers 20, 40 thus remain separate until the mixing and dispensing apparatus 10 is ready for use by the customer.

Figure 7:
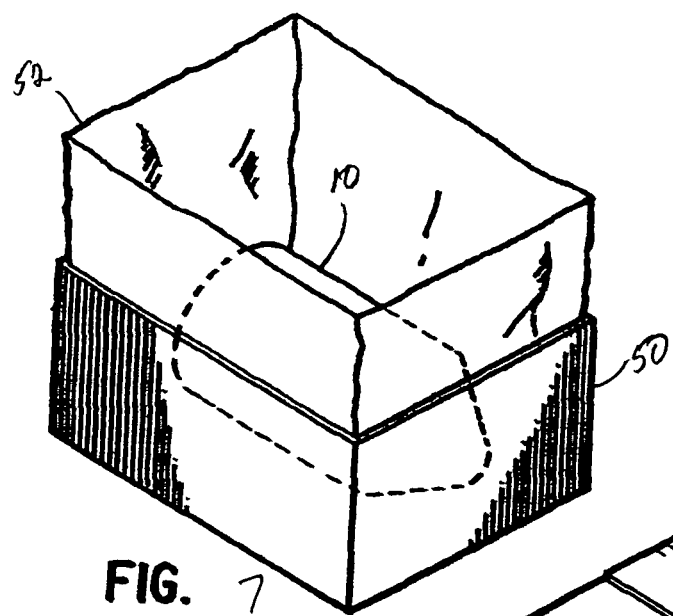
FIG. 7 is a perspective view showing the mixing and dispensing container of FIG. 1 placed in a carton having a liner.

As also shown in FIG. 1, the apparatus 10 is placed in a first sealing layer 12 and hermetically sealed by heat to form a single layer sealed enclosure. The single layer sealed enclosure can then be inserted into a second sealing layer 14 and hermetically sealed by heat to form a second layer sealed enclosure. The first and second sealing layers 12, 14 are a polyethylene composition. Turning to FIG. 7, the double layer sealed enclosure can then be inserted into a carton 50 having a plastic liner 52. The plastic liner 52 is closed by tying or the like to form a third sealing layer. Finally, the carton is closed and prepared for shipping.

Figure 8:
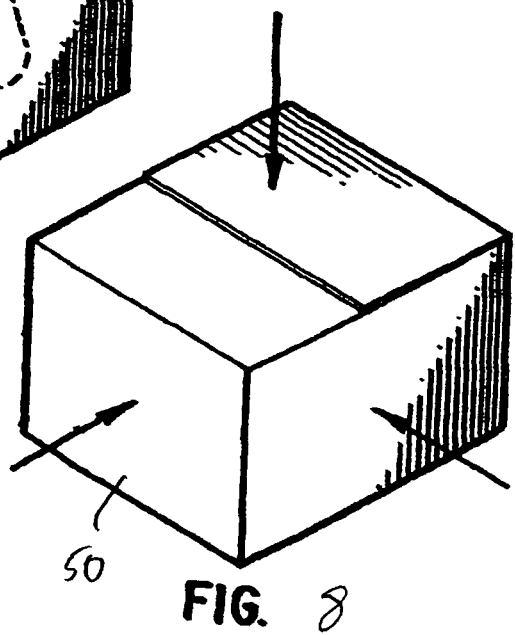
FIG. 8 is a perspective view showing the carton of FIG. 7 closed and being irradiated in a plurality of directions.

The carton is then ready for irradiation, which is shown in FIG. 8. Gamma radiation is used since it has high penetration capability that enables relatively dense products or compositions to be processed easily. Sterilizing doses generally are in the 25-50 kGy (kilogray) range. To ensure proper dosage, the radiation is measured by dosimeters that measure the amount of irradiation impinging on the carton. The irradiation sterilizes the entire packaging, including the first, second and third sealing layers, the air contained within each layer, as well as the entire apparatus 10, the chemical composition in the small container and the diluent in the large container.

In this manner, when received at the operational site, closed cartons may be opened and the liner 52 with the double-bagged chemical containers 10 contained therein may be removed on a loading dock prior to entry into a clean room area and the carton 50 discarded. The chemical containers 10 are maintained within the closed third sealing layer or liner 52 until removed and then brought to a clean room operating site. The liner is used in the preferred embodiment to prevent carton particles from contaminating the outermost sealing layer 14. Depending on the particular application, the carton liner 52 need not be used, e.g., when sterility of the exterior of the sealing layer 14 is of no concern.

Once transported into the clean room area or other operational site, third sealing layer may be removed and the container 10 within the first and second sealing layer enclosures 12, 14 may be placed on a shelf for future use. When placing the sealed container enclosures on the shelves for use in clean rooms, generally sterilized gloves are used, however, these in themselves as well as the atmosphere of clean rooms have various particulates, such as microbes or bacteria, which dictate a relatively short shelf life for container 10 if only a single first layer 24 were formed around the container 10. However, with the first and second layers 12 and 14, the now somewhat less than sterilized second layer sealed container enclosure may be kept on the shelf for an indefinite period of time prior to use of the contents of the container 10.

Once the contents of the container 10 are to be used, second sealing layer 14 may be stripped from the second layer sealed container enclosure leaving first layer 12 surrounding and encasing the container 10 in a sterilized manner. Use then can be made of the contents of container 10 with the assurance that such has been maintained in a sterilized state.

At this point, the user can use the contents of the containers 20, 40, which are sterile, as follows. The cap 21 of the large container 20 is removed and the small container 40 is pulled upward using the ring 102 of pull 100. As the small container 40 is pulled upwardly, the nozzle cap 47 is moved to the open position, and the rubber cover 45 comes off the vent 44 and stays with pull 100. The contents of the small container 40 are thereby released into the large container 20. The user then replaces the cap 21 on the large container 20, and shakes the container 20 to further combine the contents of the two containers. The thus mixed contents can then be poured out of the large container 20 through the spout 22.

Chemical compositions can also be aseptically processed when being filled into the apparatus 10. The chemical composition can be filter sterilized, and the apparatus 10 sterilized by radiation. The composition can then be filled into the containers in a clean environment, and then placed in sterilized successive sealing layers that are hermetically sealed, and placed in a carton having a liner.

All components in the aseptic filling operation are pre-sterilized via gamma radiation and transferred to the clean (usually Class 100) aseptic filling environment, other than the composition, which is filter sterilized. In such area, all personnel are completely gowned in presterilized coveralls, hoods, boots, masks and goggles. The clean room is monitored for particulates and microbials. However, aseptic processing is generally more complicated and labor-intensive, and therefore is more appropriate for compositions that are not suitable for sterilization through irradiation, such as peracetic acid and hydrogen peroxide.

Thus, in both the terminal irradiation and the aseptic processing, the mixing occurs just prior to actual use, so that the mixture is fresh and effective. The mixture is made under sterile conditions inside the sterile container, so that the resulting mixture is sterile. In addition, the contents are measured when filled into the apparatus. Thus, the user does not have to make any measurement of the chemical composition or the diluent in the clean room, and can still be certain that the proper assay is achieved.

Any suitable configuration of the apparatus 10 can be made, without departing from the spirit and scope of the invention. For instance, the small container need not be a separate container, but can be a compartment that is integral to the large container. However, the apparatus 10 of FIGS. 1-6 is advantageous since it does not require the use of any sharp instruments for opening the small container 40, nor does it require any elements to be broken or removed to release the contents of the small container 40 into the large container 20. This avoids the possibility of any foreign particles contaminating the mixture.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents falling within the scope of the invention may be resorted to.

I claim:

1. A method of sterilizing a chemical composition comprising the steps of:
   providing a first container with a first chemical composition and a second container with a second chemical composition, wherein the first container is positioned with respect to the second container so that the first chemical composition is maintained apart from said second chemical composition, but can be combined with the second chemical composition, and wherein the first and second containers are configured to be used in a clean environment without contaminating the clean environment;
   sealing the first and second containers in a first sealing layer to form a first sealed container enclosure;
   enclosing said first sealed container enclosure in a shipping container to form a closed shipping package; and
   externally irradiating said closed shipping package at a predetermined radiation level for a predetermined time interval to simultaneously sterilize said first and second chemical compositions, said first and second containers, said first sealed container enclosure, and said closed shipping package.

2. The method of claim 1, wherein the second container is positioned inside the first container.

3. The method of claim 1, wherein the second container is integral to the first container.

4. The method of claim 1, wherein said second chemical composition comprises a disinfectant liquid.

5. The method of claim 1, wherein said first chemical composition comprises a diluent.

6. The method of claim 1, wherein said second chemical composition comprises phenol.

7. The method of claim 1, wherein said irradiating step comprises subjecting the closed shipping package to gamma radiation in the range of about 20 to 50 kilograys.

8. The method of claim 7, wherein the irradiating step comprises applying the gamma radiation to the closed shipping package in a plurality of directions.

9. The method of claim 1, wherein the first chemical composition can be released into the second container in a clean environment so as to combine the first and second chemical compositions in the clean environment.

10. The method of claim 1, further comprising opening the first container in a clean environment to release the first chemical composition into the second container so as to combine the first and second chemical compositions in the clean environment.

11. The method of claim 1, wherein the first container has a neck forming a chamber, and wherein the second container is positioned inside the neck.

12. The method of claim 1, wherein the second container is positioned inside the first container, and the first chemical composition can be combined with the second chemical composition without removing the second container from the inside of the first container.

13. The method of claim 1, wherein the clean environment is a space designed, maintained, and controlled to prevent particle and microbiological contamination of products inside the space.

14. The method of claim 1, wherein the clean environment is a clean room.

15. The method of claim 1, wherein the clean environment is a controlled environment.

16. The method of claim 1, wherein the clean environment clean room controlled environment that is designed, maintained, and controlled to prevent particle and microbiological contamination of products inside the clean room controlled environment.

17. The method of claim 1, wherein the first and second containers can be used in a clean environment without contaminating the clean environment.

18. The method of claim 1, wherein the first and second containers are designed to be used in a clean room environment without contaminating the clean environment.

19. The method of claim 1, wherein the first and second containers are not frangible.

20. The method of claim 1, wherein the first and second containers are structurally configured to be used in a clean environment without contaminating the clean environment.

21. The method of claim 1, wherein the second container has a nozzle that remains fixed to the second container as it is moved between a closed position that retains the second chemical composition and an opened position that releases the second chemical composition into the first container.

22. The method of claim 1, wherein the second container has a nozzle that is pulled to move between a closed position that retains the second chemical composition and an opened position that releases the second chemical composition into the first container.

23. A method of storing a first and second chemical composition for use in a sterile environment, said first and second chemical compositions being respectively contained in a first and second container, wherein the first and second containers are configured to be used in a clean environment without contaminating the clean environment, said first and second containers being hermetically sealed in successive first and second hermetically sealed container enclosures, and a shipping enclosure to form a closed shipping package adapted to be transported, comprising the steps of:
   removing the first and second containers and the first and second hermetically sealed container enclosures from the shipping enclosure of the closed shipping package;
   transporting the first and second containers and the first and second hermetically sealed container enclosures to the storage area;
   storing the first and second containers enclosed in the first and second hermetically sealed container enclosures in the storage area for a period of time;
   after the period of time, removing the second hermetically sealed container enclosure and transporting the first and second containers contained in the first hermetically sealed container enclosure to the sterile environment for use;
   removing the first hermetically sealed container enclosure in the sterile environment for use of the first and second chemical compositions in the sterile environment; and,
   releasing the first chemical composition from the first container into the second container to mix with the second chemical compositions in the sterile environment.

24. The method of claim 23, wherein the storage area is a sterile storage area.

25. The method of claim 23, wherein said first chemical composition is a diluent and the second chemical composition is a disinfectant, and the first and second chemical compositions are sterilized in said first and second containers by gamma radiation.

26. The method of claim 25, wherein the gamma radiation is in the range of about 20 to 50 kilograys.

27. The method of claim 23, wherein said first container is located within the second container.

28. The method of claim 23, wherein each of said first and second sealing layers is formed of a single layer of closed cell polyethylene.

29. The method of claim 23, wherein said irradiating step comprises subjecting the closed shipping package to gamma radiation in the range of about 20 to 50 kilograys.

30. A method of sterilizing a chemical composition comprising the steps of:
   providing a container having a first compartment for retaining a first chemical composition and a second compartment for retaining a second chemical composition, wherein the first compartment is positioned with respect to the second compartment so that the first chemical composition is maintained apart from said second chemical composition, but can be combined with the second chemical composition, and wherein the container is configured to be used in a clean on t without contaminating the clean environment;
   sealing the container in a first sealing layer to form a first sealed container enclosure;
   enclosing said first sealed container enclosure in a shipping container to form a closed shipping package; and
   externally irradiating said closed shipping package at a predetermined radiation level for a predetermined time interval to simultaneously sterilize said first and second chemical compositions, said container, and said first sealed container enclosure.

31. The method of claim 30, wherein said second chemical composition comprises a disinfectant liquid.

32. The method of claim 30, wherein said first chemical composition comprises a diluent.

33. The method of claim 30, wherein said second chemical composition comprises phenol.

34. The method of claim 30, wherein said irradiating step comprises subjecting the closed shipping package to gamma radiation in the range of about 20 to 50 kilograys.

35. The method of claim 34, wherein the irradiating step comprises applying the gamma radiation to the closed shipping package in a plurality of directions.

36. The method of claim 30, wherein the clean environments a space designed, maintained, and controlled to prevent particle and microbiological contamination of products inside the space.

37. The method of claim 30, wherein the clean environment comprises a clean room.

38. The method of claim 30, wherein the clean environment is a controlled environment.

39. The method of claim 30, wherein the first chemical composition can be combined with the second chemical composition without removing the second container from the inside of the first container.

40. The method of claim 30, wherein the clean environment is a clean room controlled environment that is designed, maintained, and controlled to prevent particle and microbiological contamination of products inside the clean room controlled environment.

41. The method of claim 30, wherein the container can be used in a clean environment without contaminating the clean environment.

42. The method of claim 30, wherein the container is designed to be used in a clean room environment without contaminating the clean environment.

43. The method of claim 30, wherein the container is not frangible.

44. The method of claim 30, wherein the first and second containers are structurally configured to be used in a clean environment without contaminating the clean environment.

45. A method of sterilizing a chemical composition comprising the steps of:
   providing a first container with a first chemical composition and a second container with a second chemical composition, wherein the first container is positioned with respect to the second container so that the first chemical composition is maintained apart from said second chemical composition, but can be combined with the second chemical composition, and wherein the first and second containers are structurally configured to be used in a clean environment without contaminating the clean environment, wherein the first container has a nozzle that remains fixed to the second container as it is moved between a closed position that retains the first chemical composition and an opened position that releases the first chemical composition into the second container;
   sealing the first and second containers in a first sealing layer to form a first sealed container enclosure;

enclosing said first sealed container enclosure in a shipping container to form a closed shipping package; and externally irradiating said closed shipping package at a predetermined radiation level for a predetermined time interval to simultaneously sterilize said first and second chemical compositions, said first and second containers, said first sealed container enclosure, and said closed shipping package.

46. A method of mixing a first and second composition in a sterile environment comprising:

placing said first and second chemical compositions in a respective first and second compartment, wherein the first and second containers are configured to be used in a clean environment without contaminating the clean environment;

hermetically sealing said first and second compartments in a sealing layer to form a hermetically sealed container enclosure;

irradiating the hermetically sealed container enclosure to simultaneously sterilize said first and second chemical compositions, said first and second compartments, and said hermetically sealed container enclosure to form a sterilized hermetically sealed container enclosure;

introducing the sterilized hermetically sealed container enclosure into the sterile environment;

releasing the first chemical composition from the first compartment into the second compartment, so that the first chemical composition mixes with the second chemical composition.

* * * * *